(12) United States Patent
Almario Garcia et al.

(10) Patent No.: US 7,915,284 B2
(45) Date of Patent: Mar. 29, 2011

(54) 2-ARYL-6-PHENYLIMIDAZO[1,2-A]PYRIDINE DERIVATIVES, PREPARATION THEREOF AND THERAPEUTIC USE THEREOF

(75) Inventors: Antonio Almario Garcia, Paris (FR); Patrick Lardenois, Paris (FR); Anne Olivier, Paris (FR)

(73) Assignee: Sanofi-Aventis, Paris (FR)

( * ) Notice: Subject to any disclaimer, the term of this patent is extended or adjusted under 35 U.S.C. 154(b) by 113 days.

(21) Appl. No.: 12/407,449

(22) Filed: Mar. 19, 2009

(65) Prior Publication Data
US 2009/0253735 A1 Oct. 8, 2009

Related U.S. Application Data

(63) Continuation of application No. PCT/FR2007/001517, filed on Sep. 19, 2007.

(30) Foreign Application Priority Data

Sep. 22, 2006 (FR) .................................... 06 08350

(51) Int. Cl.
A61K 31/437 (2006.01)
C07D 471/04 (2006.01)
A61P 25/00 (2006.01)
A61P 25/16 (2006.01)
A61P 25/28 (2006.01)

(52) U.S. Cl. ........................ 514/300; 546/121
(58) Field of Classification Search ................ 546/121; 514/300
See application file for complete search history.

(56) References Cited

FOREIGN PATENT DOCUMENTS

| JP | 2001035664 | * | 2/2001 |
|---|---|---|---|
| WO | WO 01/74813 | | 10/2001 |
| WO | WO 2004/026867 | | 4/2004 |
| WO | WO 2004/072050 | | 8/2004 |
| WO | WO 2005/086808 | | 9/2005 |

OTHER PUBLICATIONS

Enguehard, C., et. al., (Hetero)Arylation of 6-Halogenoimidazo [1,2-a]Pyridines Differently Substituted at C(2): Influence of the 2-Substituent on the Suzuki Cross-Coupling Reaction, Helvetica Chimica Acta, vol. 84, (2001).

Wang, Z., et. al., Structute and Function of Nurr1 Identifies a Class of Ligand-Independent Nuclear Receptors, Nature vol. 423, 555-560, (2003).

* cited by examiner

*Primary Examiner* — D. Margaret Seaman
*Assistant Examiner* — Niloofar Rahmani
(74) *Attorney, Agent, or Firm* — Jiang Lin

(57) ABSTRACT

The present invention is related to a compound of formula (I)

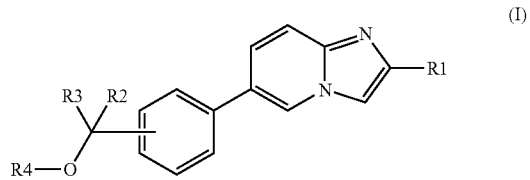

wherein $R_1$, $R_2$, $R_3$ and $R_4$ are as defined herein, or an addition salt of an acid thereof, the pharmaceutical composition and preparation thereof, and the therapeutic use thereof in the treatment or the prevention of diseases involving Nurr-1 nuclear receptors, also known as NR4A2, NOT, TINUR, RNR-1 and HZF3.

17 Claims, No Drawings

2-ARYL-6-PHENYLIMIDAZO[1,2-A]PYRIDINE DERIVATIVES, PREPARATION THEREOF AND THERAPEUTIC USE THEREOF

This application is a Continuation of International Application No. PCT/FR2007/001517, filed Sep. 19, 2007, which is incorporated herein by reference in its entirety.

The present invention relates to 2-aryl-6-phenylimidazo[1,2-a]pyridine derivatives, to the preparation thereof and to the therapeutic use thereof in the treatment or the prevention of diseases involving Nurr-1 nuclear receptors, also known as NR4A2, NOT, TINUR, RNR-1 and HZF3.

A subject of the present invention is the compounds corresponding to formula (I):

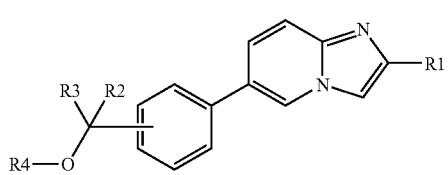

in which:

$R_1$ is:
a phenyl group or a naphthyl group, it being possible for these two groups to be optionally substituted with one or more atoms or groups selected, independently of one another, from the following atoms or groups: halogen, $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, $(C_3-C_7)$cycloalkoxy, $(C_3-C_7)$cycloalkyl$(C_1-C_3)$alkyleneoxy, halo$(C_1-C_6)$alkoxy, $(C_1-C_6)$thioalkyl, —S(O)$(C_1-C_6)$alkyl, —S(O)$_2$$(C_1-C_6$-alkyl), hydroxyl, cyano, nitro, hydroxy$(C_1-C_6)$alkylene, NRaRb$(C_1-C_6)$alkylene, $(C_1-C_6)$alkoxy$(C_1-C_6)$alkyleneoxy, NRaRb, CONRaRb, SO$_2$NRaRb, NRcCORd, OC(O)NRaRb, NRcC(O)ORe, NRcSO$_2$Re, aryl$(C_1-C_6)$alkylene, aryl or heteroaryl, the aryl or the heteroaryl being optionally substituted with one or more substituents selected from a halogen, or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group;

$R_2$ and $R_3$ are, independently of one another,
a hydrogen atom,
a $(C_1-C_6)$alkyl, $(C_3-C_7)$cycloalkyl or $(C_3-C_7)$cycloalkyl$(C_1-C_3)$alkylene group, this group being optionally substituted with an Rf group;
an aryl group, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group;

$R_4$ is:
a hydrogen atom,
a $(C_1-C_6)$alkyl, $(C_3-C_7)$cycloalkyl or $(C_3-C_7)$cycloalkyl$(C_1-C_3)$alkylene group, this group being optionally substituted with an Rf group;
an aryl group, the aryl being optionally substituted with one or more substituents chosen from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, $(C_3-C_7)$cycloalkoxy, $(C_3-C_7)$cycloalkyl$(C_1-C_3)$alkyleneoxy, halo$(C_1-C_6)$alkoxy, NRaRb, hydroxyl, nitro, cyano, $(C_1-C_6)$alkyl(CO)—, CONRaRb, NRcCORd, OC(O)N-RaRb, NRcC(O)ORe or aryl group, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group;

Ra and Rb are, independently of one another,
a hydrogen atom or a $(C_1-C_6)$alkyl, $(C_3-C_7)$cycloalkyl, $(C_3-C_7)$cycloalkyl$(C_1-C_3)$alkylene, aryl$(C_1-C_6)$alkylene or aryl group;
or Ra and Rb form, together with the nitrogen atom which bears them, an azetidine, pyrrolidine, piperidine, azepine, morpholine, thiomorpholine, piperazine or homopiperazine group, this group being optionally substituted with a $(C_1-C_6)$alkyl, $(C_3-C_7)$cycloalkyl, $(C_3-C_7)$cycloalkyl$(C_1-C_6)$alkylene, aryl or aryl$(C_1-C_6)$alkylene group;

Rc and Rd are, independently of one another,
a hydrogen atom or a $(C_1-C_6)$alkyl, $(C_3-C_7)$cycloalkyl, $(C_3-C_7)$cycloalkyl$(C_1-C_3)$alkylene, aryl$(C_1-C_6)$alkylene and aryl group;
or Rc and Rd together form a $(C_2-C_5)$alkylene group;

Re is
a $(C_1-C_6)$alkyl, $(C_3-C_7)$cycloalkyl, $(C_3-C_7)$cycloalkyl$(C_1-C_3)$alkylene,
aryl$(C_1-C_6)$alkylene and aryl group;
or Rc and Re together form a $(C_2-C_5)$alkylene group;

Rf is
a halogen atom or a $(C_1-C_6)$alkoxy, halo$(C_1-C_6)$alkoxy, $(C_3-C_7)$cycloalkoxy, $(C_3-C_7)$cycloalkyl$(C_1-C_6)$alkyleneoxy, hydroxyl, cyano, NRaRb, C(O)NRaRb, NRcCORd, OC(O)NRaRb, NRcCOORe, SO$_2$NRaRb, NRcSO$_2$Re, aryl$(C_1-C_6)$alkylene or aryl group, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group;

in the form of a base or of an addition salt with an acid.

The compounds of formula (I) can contain one or more asymmetrical carbon atoms. They can therefore exist in the form of enantiomers or of diastereoisomers. These enantiomers and diastereoisomers, and also mixtures thereof, including racemic mixtures, are part of the invention.

In the various groups as defined below, the groups Ra, Rb, Rc, Rd, Re and Rf have the same definitions as those mentioned above.

Among the compounds of formula (I) which are subjects of the invention, a first group of compounds in the form of a base or of an addition salt with an acid comprises compounds for which:

$R_1$ is a naphthyl group or a phenyl group which can be optionally substituted with one or more atoms or groups selected, independently of one another, from the following atoms or groups: halogen, $(C_1-C_6)$alkyl, $(C_3-C_7)$cycloalkyl, $(C_3-C_7)$cycloalkyl$(C_1-C_6)$alkylene, $(C_1-C_6)$alkoxy, $(C_3-C_7)$cycloalkyl$(C_1-C_6)$alkoxy, hydroxy, cyano, nitro, NRaRb, hydroxy$(C_1-C_6)$alkyl, $(C_1-C_6)$alkoxy$(C_1-C_6)$alkyl, halo$(C_1-C_6)$alkyl, halo$(C_1-C_6)$alkoxy or aryl, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group.

Among the compounds of formula (I) which are subjects of the invention, a second group of compounds in the form of a base or of an addition salt with an acid comprises compounds for which:

$R_2$ and $R_3$ are, independently of one another,
a hydrogen atom,
a $(C_1-C_6)$alkyl, $(C_3-C_7)$cycloalkyl or $(C_3-C_7)$cycloalkyl$(C_1-C_3)$alkylene group
optionally substituted with an Rf group;
$R_4$ is:
a hydrogen atom,
a $(C_1-C_6)$alkyl, $(C_3-C_7)$cycloalkyl or $(C_3-C_7)$cycloalkyl$(C_1-C_3)$alkylene group optionally substituted with an Rf group,
an aryl group optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, $(C_3-C_7)$cycloalkoxy, $(C_3-C_7)$cycloalkyl$(C_1-C_3)$alkyleneoxy, halo$(C_1-C_6)$alkoxy, NRaRb, hydroxyl, nitro, cyano, $(C_1-C_6)$alkyl(CO)—, NRcCORd or aryl group, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group.

Among the compounds of formula (I) which are subjects of the invention, a third group of compounds in the form of a base or of an addition salt with an acid comprises compounds for which:
the substituent

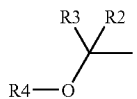

is in the meta-position on the phenyl.

Among the compounds of formula (I) which are subjects of the invention, a fourth group of compounds in the form of a base or of an addition salt with an acid comprises compounds for which:
$R_4$ is a hydrogen atom and $R_2$, $R_3$ are, independently of one another, a hydrogen atom or a $(C_1-C_6)$alkyl, $(C_3-C_7)$cycloalkyl or $(C_3-C_7)$cycloalkyl$(C_1-C_3)$alkylene group optionally substituted with an Rf group.

Among the compounds of formula (I) which are subjects of the invention, a fifth group of compounds in the form of a base or of an addition salt with an acid comprises compounds for which:
$R_1$ is a naphthyl group or a phenyl group which can be optionally substituted with one or more atoms or groups selected, independently of one another, from the following atoms or groups: halogen, $(C_1-C_6)$alkyl, $(C_3-C_7)$cycloalkyl, $(C_3-C_7)$cycloalkyl$(C_1-C_6)$alkylene, $(C_1-C_6)$alkoxy, $(C_3-C_7)$cycloalkyl$(C_1-C_6)$alkoxy, hydroxyl, cyano, nitro, NRaRb, hydroxy$(C_1-C_6)$alkyl, $(C_1-C_6)$alkoxy$(C_1-C_6)$alkyl, halo$(C_1-C_6)$alkyl, halo$(C_1-C_6)$alkoxy or aryl, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group;
$R_2$ and $R_3$ are, independently of one another,
a hydrogen atom,
a $(C_1-C_6)$alkyl, $(C_3-C_7)$cycloalkyl or $(C_3-C_7)$cycloalkyl$(C_1-C_3)$alkylene group, this group being optionally substituted with an Rf group;
an aryl group, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group;
$R_4$ is:
a hydrogen atom,
a $(C_1-C_6)$alkyl, $(C_3-C_7)$cycloalkyl or $(C_3-C_7)$cycloalkyl$(C_1-C_3)$alkylene group, this group being optionally substituted with an Rf group,
an aryl group, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, nitro, cyano, $(C_1-C_6)$alkyl(CO)— or NRcCORd group.

Among the compounds of formula (I) which are subjects of the invention, a sixth group of compounds in the form of a base or addition salt with an acid comprises compounds for which:
$R_1$ is a naphthyl group or a phenyl group which can be optionally substituted with one or more atoms or groups selected, independently of one another, from the following atoms or groups: halogen, $(C_1-C_6)$alkyl, $(C_3-C_7)$cycloalkyl, $(C_3-C_7)$cycloalkyl$(C_1-C_6)$alkylene, $(C_1-C_6)$alkoxy, $(C_3-C_7)$cycloalkyl$(C_1-C_6)$alkoxy, hydroxyl, cyano, nitro, NRaRb, hydroxy$(C_1-C_6)$alkyl, $(C_1-C_6)$alkoxy$(C_1-C_6)$alkyl, halo$(C_1-C_6)$alkyl or halo$(C_1-C_6)$alkoxy,
$R_2$ and $R_3$ are, independently of one another,
a hydrogen atom,
a $(C_1-C_6)$alkyl, $(C_3-C_7)$cycloalkyl or $(C_3-C_7)$cycloalkyl$(C_1-C_3)$alkylene group, this group being optionally substituted with an Rf group;
an aryl group, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano group;
$R_4$ is:
a hydrogen atom,
a $(C_1-C_6)$alkyl, $(C_3-C_7)$cycloalkyl or $(C_3-C_7)$cycloalkyl$(C_1-C_3)$alkylene group, this group being optionally substituted with an Rf group,
an aryl group, the aryl being optionally substituted with one or more substituents selected from a halogen or a $(C_1-C_6)$alkyl, $(C_3-C_7)$cycloalkyl, $(C_3-C_7)$cycloalkyl$(C_1-C_3)$alkylene, halo$(C_1-C_6)$alkyl, nitro, cyano, $(C_1-C_6)$alkyl(CO)— or NRcCORd group.

The combinations of the groups one to six as defined above are also part of the invention.

The compounds of formula (I) can exist in the form of bases or of addition salts with acids. Such addition salts are part of the invention.

These salts can be prepared with pharmaceutically acceptable acids, but the salts of other acids useful, for example, for the purification or the isolation of the compounds of formula (I) are also part of the invention.

The compounds of formula (I) can also exist in the form of hydrates or of solvates, i.e. in the form of associations or combinations with one or more molecules of water or with a solvent. Such hydrates and solvates are also part of the invention.

In the context of the present invention:
the term "a halogen atom" is intended to mean: a fluorine, a chlorine, a bromine or an iodine;
the term "a $(C_1-C_6)$alkyl group" is intended to mean: a linear or branched, saturated aliphatic group containing from 1 to 6 carbons. By way of examples, mention may be made of methyl, ethyl, propyl, isopropyl, butyl, isobutyl, tert-butyl, pentyl, etc., groups;

the term "a ($C_3$-$C_7$)cycloalkyl group" is intended to mean: a cyclic carbon-based group containing from 3 to 7 carbons. By way of examples, mention may be made of cyclopropyl, cyclobutyl, cyclopentyl, cyclohexyl, etc., groups;

the term "an alkylene" is intended to mean: a linear or branched, saturated divalent alkyl group; for example, a ($C_1$-$C_6$)alkylene group is a linear or branched, divalent carbon-based chain containing from 1 to 6 carbon atoms, more particularly a methylene, ethylene, 1-methylethylene or propylene;

the term "a ($C_1$-$C_6$)alkoxy group" is intended to mean: an —O-alkyl radical where the alkyl group is as defined above;

the term "($C_3$-$C_7$)cycloalkoxy group" is intended to mean: an —O-cycloalkyl radical where the cycloalkyl group is as defined above;

the term "a halo($C_1$-$C_6$)alkyl group" is intended to mean: a linear, branched or cyclic, saturated aliphatic group containing from 1 to 6 carbon atoms which is substituted with one or more identical or different halogen atoms. By way of examples, mention may be made of $CF_3$, $CH_2CF_3$, $CHF_2$ or $CCl_3$ groups;

the term "a halo($C_1$-$C_6$)alkoxy group" is intended to mean: an —O-alkyl radical where the alkyl group is as defined above and which is substituted with one or more identical or different halogen atoms. By way of examples, mention may be made of $OCF_3$, $OCHF_2$ or $OCCl_3$ groups;

the term "a thioalkyl group" is intended to mean: an S-alkyl radical where the alkyl group is as defined above;

the sulphur and nitrogen atoms can be in the oxidized state (N-oxide, sulphoxide, sulphone);

the term "an aryl" is intended to mean: a cyclic aromatic group comprising between 6 and 10 carbon atoms. By way of examples of aryl groups, mention may be made of phenyl or naphthyl groups;

the term "a heteroaryl" is intended to mean: an aromatic cyclic group having from 5 to 10 ring members containing from 1 to 4 heteroatoms selected from O, S or N. By way of nonlimiting example, mention may be made of imidazolyl, thiazolyl, oxazolyl, furanyl, thiophenyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl, benzotriazolyl, quinolinyl, isoquinolinyl or quinoxalinyl groups.

Among the compounds of formula (I) which are subjects of the invention, mention may be made of the following compounds:

[4-(2-phenylimidazo[1,2-a]pyridin-6-yl)phenyl]methanol
[3-(2-phenylimidazo[1,2-a]pyridin-6-yl)phenyl]methanol
{4-[2-(4-pyrrolidin-1-ylphenyl)imidazo[1,2-a]pyridin-6-yl]phenyl}methanol
[4-(2-biphenyl-4-ylimidazo[1,2-a]pyridin-6-yl)phenyl]methanol
3-[6-(4-hydroxymethylphenyl)imidazo[1,2-a]pyridin-2-yl]benzonitrile
3-[6-(3-hydroxymethylphenyl)imidazo[1,2-a]pyridin-2-yl]benzonitrile
3-{6-[3-(2-methoxyethoxymethyl)phenyl]imidazo[1,2-a]pyridin-2-yl}benzonitrile
4-[6-(3-hydroxymethylphenyl)imidazo[1,2-a]pyridin-2-yl]benzonitrile
{3-[2-(naphthalen-2-yl)imidazo[1,2-a]pyridin-6-yl]phenyl}methanol
[3-(2-p-tolylimidazo[1,2-a]pyridin-6-yl)phenyl]methanol
{3-[2-(4-pyrrolidin-1-ylphenyl)imidazo[1,2-a]pyridin-6-yl]phenyl}methanol
{3-[2-(3-trifluoromethoxyphenyl)imidazo[1,2-a]pyridin-6-yl]phenyl}methanol
{3-[2-(4-nitrophenyl)imidazo[1,2-a]pyridin-6-yl]phenyl}methanol
{4-[2-(4-diethylaminophenyl)imidazo[1,2-a]pyridin-6-yl]phenyl}methanol
[3-(2-naphthalen-1-ylimidazo[1,2-a]pyridin-6-yl)phenyl]methanol
{3-[2-(2,4-dimethylphenyl)imidazo[1,2-a]pyridin-6-yl]phenyl}methanol
6-[3-(2-methoxyethoxymethyl)phenyl]-2-naphthalen-2-ylimidazo[1,2-a]pyridine
{3-[2-(4-methoxyphenyl)imidazo[1,2-a]pyridin-6-yl]phenyl}methanol
{3-[2-(3-methoxyphenyl)imidazo[1,2-a]pyridin-6-yl]phenyl}methanol
{3-[2-(2-methoxyphenyl)imidazo[1,2-a]pyridin-6-yl]phenyl}methanol
{3-[2-(2,4-dimethoxyphenyl)imidazo[1,2-a]pyridin-6-yl]phenyl}methanol
{3-[2-(4-fluorophenyl)imidazo[1,2-a]pyridin-6-yl]phenyl}methanol
{3-[2-(3,5-difluorophenyl)imidazo[1,2-a]pyridin-6-yl]phenyl}methanol
{3-[2-(3-fluoro-5-trifluoromethylphenyl)imidazo[1,2-a]pyridin-6-yl]phenyl}methanol
{3-[2-(4-chlorophenyl)imidazo[1,2-a]pyridin-6-yl]phenyl}methanol
{3-[2-(4-chlorophenyl)imidazo[1,2-a]pyridin-6-yl]phenyl}methanol hydrochloride (1:1)
{3-[2-(3-chlorophenyl)imidazo[1,2-a]pyridin-6-yl]phenyl}methanol
{3-[2-(4-chloro-3-methylphenyl)imidazo[1,2-a]pyridin-6-yl]phenyl}methanol
{3-[2-(3,4-dichlorophenyl)imidazo[1,2-a]pyridin-6-yl]phenyl}methanol
{3-[2-(3-fluorophenyl)imidazo[1,2-a]pyridin-6-yl]phenyl}methanol
6-[3-(4-chlorophenoxymethyl)phenyl]-2-p-tolylimidazo[1,2-a]pyridine
N-{4-[3-(2-p-tolylimidazo[1,2-a]pyridin-6-yl)benzyloxy]phenyl}acetamide
6-[3-(3-nitrophenoxymethyl)phenyl]-2-p-tolylimidazo[1,2-a]pyridine
6-[3-(4-methylphenoxymethyl)phenyl]-2-p-tolylimidazo[1,2-a]pyridine
4-[3-(2-p-tolylimidazo[1,2-a]pyridin-6-yl)benzyloxy]benzonitrile
1-{4-[3-(2-p-tolylimidazo[1,2-a]pyridin-6-yl)benzyloxy]phenyl}ethanone
6-[3-(4-trifluoromethylphenoxymethyl)phenyl]-2-p-tolylimidazo[1,2-a]pyridine
{3-[2-(3-fluoro-4-methylphenyl)imidazo[1,2-a]pyridin-6-yl]phenyl}methanol
2-{3-[2-(4-chlorophenyl)imidazo[1,2-a]pyridin-6-yl]phenyl}propan-2-ol
{2-[2-(4-chlorophenyl)imidazo[1,2-a]pyridin-6-yl]phenyl}methanol
{2-[2-(4-chlorophenyl)imidazo[1,2-a]pyridin-6-yl]phenyl}methanol hydrochloride (1:1)
racemic 1-{3-[2-(4-chlorophenyl)imidazo[1,2-a]pyridin-6-yl]phenyl}ethanol
{3-[2-(2,4-dichlorophenyl)imidazo[1,2-a]pyridin-6-yl]phenyl}methanol {3-[2-(2,4-difluorophenyl)imidazo[1,2-a]pyridin-6-yl]
  phenyl}methanol
{3-[2-(3,4-difluorophenyl)imidazo[1,2-a]pyridin-6-yl]
  phenyl}methanol
{3-[2-(3,4-difluorophenyl)imidazo[1,2-a]pyridin-6-yl]
  phenyl}methanol hydrochloride (1:1)
{3-[2-(2-chloro phenyl)imidazo[1,2-a]pyridin-6-yl]
  phenyl}methanol
{3-[2-(4-trifluoromethylphenyl)imidazo[1,2-a]pyridin-6-yl]
  phenyl}methanol
{3-[2-(4-(difluoromethyl)phenyl)imidazo[1,2-a]pyridin-6-
  yl]phenyl}methanol racemic 1-{2-[2-(4-chlorophenyl)
  imidazo[1,2-a]pyridin-6-yl]phenyl}ethanol
2-(4-chlorophenyl)-6-(2-methoxymethylphenyl)imidazo[1,
  2-a]pyridine
2-(4-chlorophenyl)-6-(2-methoxymethylphenyl)imidazo[1,
  2-a]pyridine hydrochloride (1:1)
2-(4-chlorophenyl)-6-(4-methoxymethylphenyl)imidazo[1,
  2-a]pyridine racemic 1-{3-[2-(4-chlorophenyl)imidazo[1,2-a]pyridin-6-
  yl]phenyl}propan-1-ol
racemic 1-{3-[2-(4-chlorophenyl)imidazo[1,2-a]pyridin-6-
  yl]phenyl}pentan-1-ol
racemic 1-{3-[2-(4-chlorophenyl)imidazo[1,2-a]pyridin-6-
  yl]phenyl} heptan-1-ol
racemic 1-{3-[2-(4-chlorophenyl)imidazo[1,2-a]pyridin-6-
  yl]phenyl}-3-methylbutan-1-ol
racemic {3-[2-(4-chlorophenyl)imidazo[1,2-a]pyridin-6-yl]
  phenyl}cyclopentylmethanol
racemic {3-[2-(4-chlorophenyl)imidazo[1,2-a]pyridin-6-yl]
  phenyl}phenylmethanol dextrorotatory enantiomer of
  1-{3-[2-(4-chlorophenyl)imidazo[1,2-a]pyridin-6-yl]
  phenyl}ethanol
levorotatory enantiomer of 1-{3-[2-(4-chlorophenyl)imidazo
  [1,2-a]pyridin-6-yl]phenyl}ethanol
2-(4-chlorophenyl)-6-(3-methoxymethylphenyl)imidazo[1,
  2-a]pyridine
racemic 1-{4-[2-(4-chlorophenyl)imidazo[1,2-a]pyridin-6-
  yl]phenyl}ethanol
racemic 1-{3-[2-(2,4-difluorophenyl)imidazo[1,2-a]pyridin-
  6-yl]phenyl}ethanol racemic 1-{3-[2-(4-fluorophenyl)imidazo[1,2-a]pyridin-6-
  yl]phenyl}ethanol
racemic 1-{3-[2-(3,4-difluorophenyl)imidazo[1,2-a]pyridin-
  6-yl]phenyl}ethanol
racemic 1-{3-[2-(2-chlorophenyl)imidazo[1,2-a]pyridin-6-
  yl]phenyl}ethanol
racemic 1-{3-[2-(3-fluorophenyl)imidazo[1,2-a]pyridin-6-
  yl]phenyl}ethanol
racemic 1-{3-[2-(3-chlorophenyl)imidazo[1,2-a]pyridin-6-
  yl]phenyl}ethanol
4-[6-(3-hydroxymethylphenyl)imidazo[1,2-a]pyridin-2-yl]
  phenol.

In accordance with the invention, the compounds of general formula (I) can be prepared according to the process described in scheme 1.

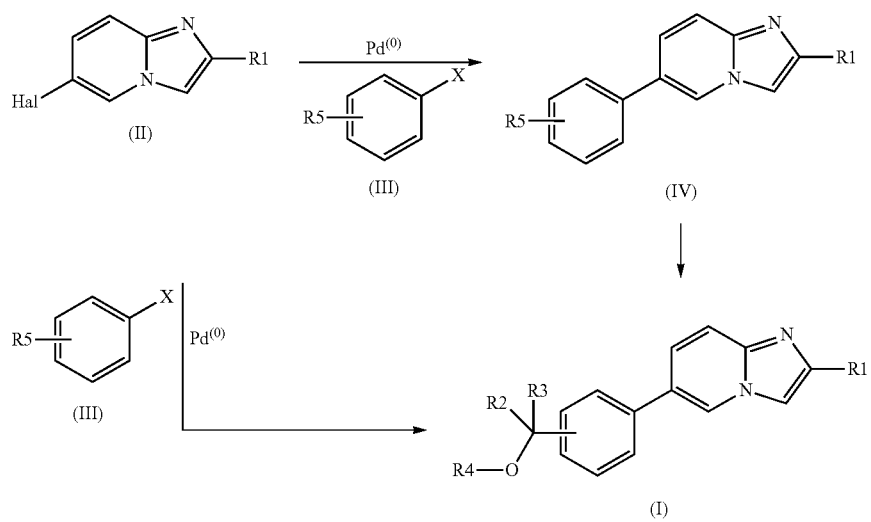

Scheme 1

The compounds of the invention can be prepared according to scheme 1 by means of a coupling reaction, catalysed by a metal such as palladium, between a 2-arylimidazopyridine of general formula (II), in which R1 is defined as above and Hal is a halogen atom, and a derivative of general formula (III) in which X is a derivative of boron or of tin and R5 is the group

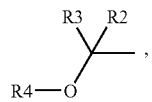

so as to obtain the compounds of general formula (I).
The compounds of the invention can also be prepared according to scheme 1 by means of a coupling reaction, catalysed by a metal such as palladium, between a 2-arylimidazopyridine of general formula (II), in which R1 is as defined above and Hal is a halogen atom, and a derivative of general formula (III) in which X is a derivative of boron or of tin and R5 is a carbonylated derivative R2COR3, in which R2 and R3 are defined as above, so as to obtain the compounds of general formula (IV), for example according to the method described by A. Gueiffier in *Helv. Chim. Acta* 2001, 84, 3610-3615.

Next, the compounds of general formula (IV) can be converted to compounds of general formula (I) through the action of an organometallic derivative such as an organomagnesium compound, or by reduction of the carbonyl group by means of a metal hydride, for example sodium borohydride or one of its derivatives, or any other method known to those skilled in the art.

The products of formula (I) can be subjected, if desired and if necessary, to any reactions known to those skilled in the art, in any order, in order to be converted to other products of formula (I).

By way of examples of reactions, mention may be made of: acid-function esterification or amidation reactions, carbamoylation reactions, ester-function hydrolysis reactions, reactions to convert a hydroxyl function to an alkoxy function, coupling reactions catalysed by a transition metal, reactions for protecting reactive functions, reactions for eliminating protective groups that may bear the protected reactive functions, salification reactions with an inorganic or organic acid or with a base in order to obtain the corresponding salt, reactions for resolving racemic forms into enantiomers, said products of formula (I) thus obtained being, where appropriate, in any of the possible racemic, enantiomer and diastereoisomer isomeric forms.

In scheme 1, the starting compounds and the reactants, when the method for preparing them is not described, are commercially available or described in the literature, or else can be prepared according to methods which are described therein or which are known to those skilled in the art.

The following examples describe the preparation of certain compounds in accordance with the invention. These examples are not limiting and merely illustrate the present invention. The numbers of the compounds exemplified refer to those given in the tables hereinafter, which illustrate the chemical structures and the physical characteristics of some compounds according to the invention.

The naming of the compounds was established based on the Autonom software.

EXAMPLE 1

[4-(2-Phenylimidazo[1,2-a]pyridin-6-yl)phenyl]methanol (Compound 1 of the Table)

1.1 6-Bromo-2-phenylimidazo[1,2-a]pyridine 1.99 g of 2-bromo-1-phenylethanone, 1.73 g of 2-amino-5-bromopyridine and 1 g of sodium hydrogen carbonate in a mixture of 20 ml of ethanol and 5 ml of water are placed in a round-bottomed flask. The mixture is heated at 80° C. for 4 h and left to cool and 40 ml of water are added. The mixture is stirred for 15 min and the precipitate is then recovered by filtration; it is washed with water and then with diisopropyl ether and dried in a desiccator. 1.8 g of compound are obtained. Mp=192-194° C.

1.2 [4-(2-Phenylimidazo[1,2-a]pyridin-6-yl)phenyl]methanol 150 mg of 6-bromo-2-phenylimidazo[1,2-a]pyridine, 125 mg of 4-(hydroxymethyl)phenylboronic acid, 19 mg of tetrakis(triphenylphosphine)palladium and 2 ml of acetonitrile are placed in a microwave tube. Under a stream of nitrogen, 2 ml of nitrogen-degassed toluene and then 2 ml of a 2M solution of sodium carbonate are added thereto. The tube is placed in a microwave device and irradiated at 150° C. for 15 min. The organic phase is recovered, dried and then concentrated under reduced pressure. The residue is taken up with diisopropyl ether and the precipitate is recovered by filtration, washed and dried. It is purified by recrystallization from n-butanol. 52 mg of compound are obtained. Mp=238-240° C. 1H NMR (DMSO-d6, δ in ppm): 4.54 (d, J=5.5 Hz, 2H); 5.2 (t, J=5.6 Hz, 1H); from 7.24 to 7.73 (m, 9H); 7.96 (m, 2H); 8.36 (s, 1H); 8.84 (t, J=1.3 Hz, 1H). M+H=301.

EXAMPLE 2

[3-(2-(Naphthalen-2-yl)imidazo[1,2-a]pyridin-6-yl)phenyl]methanol (Compound 9 of the Table)

2.1 6-Bromo-2-(naphthalen-2-yl)imidazo[1,2-a]pyridine

By carrying out the process as in Example 1, and starting from 0.5 g of 2-bromo-1-(naphthalen-2-yl)ethanone, 0.72 g of 2-amino-5-bromopyridine and 0.29 g of sodium hydrogen carbonate, 0.83 g of 6-bromo-2-(naphthalen-2-yl)imidazo[1,2-a]pyridine is obtained. Mp=226-228° C.

2.2 [3-(2-(Naphthalen-2-yl)imidazo[1,2-a]pyridin-6-yl)phenyl]methanol

Under a stream of nitrogen, 500 mg of 6-bromo-2-(naphthalen-2-yl)imidazo[1,2-a]pyridine, 235 mg of 3-(hydroxymethyl)phenylboronic acid and 90 mg of tetrakis(triphenylphosphine)palladium are placed in a microwave tube containing 5 ml of toluene degassed beforehand under a stream of nitrogen, 5 ml of acetonitrile and 6 ml of a 0.5M solution of sodium carbonate. The tube is placed in a microwave apparatus and irradiated at 150° C. for 15 min. The organic phase is separated and dried and the filtrate is concentrated under reduced pressure. The residue obtained is taken up with 5 ml of dichloromethane. A precipitate forms and is recovered by filtration, washed with dichloromethane and then with diisopropyl ether and dried under reduced pressure. The experiment is repeated several times (6) and the solids are combined. 2.2 g of compound are obtained and are recrystallized from a 1/1 n-propanol/water mixture. The precipitate is filter-dried, washed with diisopropyl ether and dried under reduced pressure. 1.96 g of compound are obtained. Mp=161-163° C. 1H NMR (DMSO-d6, δ in ppm): 4.58 (d, J=5.5 Hz, 2H); 5.24 (t, J=5.7 Hz, 1H); from 7.29 to 7.73 (m, 8H); from 7.86 to 8.13 (m, 4H); 8.52 (m, 2H); 8.84 (m, 1H). M+H=351.

EXAMPLE 3

[3-(2-p-Tolylimidazo[1,2-a]pyridin-6-yl)phenyl]methanol (Compound 10 of the Table)

3.1 6-Bromo-2-p-tolylimidazo[1,2-a]pyridine

By carrying out the process as in Example 1, starting from 150 mg of 2-bromo-1-p-tolylethanone, 185 mg of 2-amino-5-bromopyridine and 87 mg of sodium hydrogen carbonate, 200 mg of 6-bromo-2-p-tolylimidazo[1,2-a]pyridine are obtained. The compound is purified by silica gel chromatography, elution being carried out with a 98/2 dichloromethane/methanol mixture. 60 mg of compound are obtained. Mp=226-228° C.

3.2 [3-(2-p-Tolylimidazo[1,2-a]pyridin-6-yl)phenyl]methanol

Under a stream of nitrogen, 200 mg of 6-bromo-2-p-tolylimidazo[1,2-a]pyridine, 160 mg of 3-(hydroxymethyl)

phenylboronic acid and 24 mg of tetrakis(triphenylphosphine)palladium are placed in a microwave tube containing 2 ml of toluene degassed beforehand under a stream of nitrogen, 2 ml of acetonitrile and 2 ml of a 2M solution of sodium carbonate. The tube is placed in a microwave apparatus and irradiated at 150° C. for 15 min. The organic phase is separated and dried and the filtrate is concentrated under reduced pressure. The residue obtained is taken up with 6 ml of dichloromethane. The precipitate is recovered by filtration, washed with dichloromethane and dried in a desiccator under reduced pressure. 100 mg of compound are obtained. Mp=171-173° C. 1H NMR (DMSO-d6, δ in ppm): 2.32 (s, 3H); 4.57 (d, J=5.6 Hz, 2H); 5.23 (t, J=5.7 Hz, 1H); from 7.19 to 7.67 (m, 8H); 7.84 (d, J=8 Hz, 2H); 8.32 (s, 1H); 8.82 (m, 1H). M+H=315.

EXAMPLE 4

6-[3-(2-Methoxyethoxymethyl)phenyl]-2-(naphthalen-2-yl)imidazo[1,2-a]pyridine (Compound 17 of the Table)

100 mg of [3-(2-naphthalen-2-ylimidazo[1,2-a]pyridin-6-yl)phenyl]methanol (Example 2) and 120 mg of 2-bromoethanol methyl ether are dissolved in 5 ml of a 1/1 methanol/dimethylformamide mixture, in a pressure tube, and 1 g of potassium fluoride on alumina is added thereto. The tube is closed and heated for 16 h at 80° C. After cooling, the mineral is removed by filtration and washed with dichloromethane. The filtrate is concentrated under reduced pressure and purified by silica gel chromatography, elution being carried out with a 99/1 dichloromethane/methanol mixture. An oil which crystallizes from 5 ml of diisopropyl ether is obtained. The precipitate is recovered by filtration, washed with diisopropyl ether and dried under reduced pressure. 44 mg of compound are obtained. Mp=80-82° C. 1H NMR (DMSO-d6, δ in ppm): 3.25 (m, 3H) 3.55 (m, 4H); 4.57 (s, 2H); from 7.27 to 7.80 (m, 8H); from 7.82 to 8.16 (m, 4H); 8.52 (m, 2H); 8.89 (m, 1H). M+H=409.

EXAMPLE 5

{3-[2-(4-Chlorophenyl)imidazo[1,2-a]pyridin-6-yl]phenyl}methanol (Compound 25 of the Table)

5.1
6-Bromo-2-(4-chlorophenyl)imidazo[1,2-a]pyridine

By carrying out the process as in Example 1, starting from 675 mg of 2-bromo-1-(4-chlorophenyl)ethanone, 500 mg of 2-amino-5-bromopyridine and 290 mg of sodium hydrogen carbonate, 680 mg of 6-bromo-2-(4-chlorophenyl)imidazo[1,2-a]pyridine are obtained. The compound is purified by silica gel chromatography, elution being carried out with a 98/2 dichloromethane/methanol mixture. 60 mg of compound are obtained. Mp=210-211° C.

5.2 {3-[2-(4-Chlorophenyl)imidazo[1,2-a]pyridin-6-yl]phenyl}methanol

Under a stream of nitrogen, 210 mg of 6-bromo-2-(4-chlorophenyl)imidazo[1,2-a]pyridine, 155 mg of 3-(hydroxymethyl)phenylboronic acid and 24 mg of tetrakis(triphenylphosphine)palladium are placed in a microwave tube containing 3 ml of toluene degassed beforehand under a stream of nitrogen, 3 ml of acetonitrile and 3 ml of a 2M solution of sodium carbonate. The tube is placed in a microwave apparatus and irradiated at 150° C. for 15 min. The organic phase is separated and dried and the filtrate is concentrated under reduced pressure. The residue obtained is taken up with dichloromethane. The precipitate is recovered by filtration, washed with dichloromethane and dried in a desiccator under reduced pressure. 175 mg of compound are obtained. Mp=181-182° C. 1H NMR (DMSO-d6, δ in ppm): 4.57 (d, J=5.5 Hz, 2H); 5.23 (t, J=5.6 Hz, 1H); from 7.28 to 7.71 (m, 8H); 7.97 (m, J=8.5 Hz, 2H); 8.41 (s, 1H); 8.84 (m, 1H). M+H=335.

EXAMPLE 6

{3-[2-(4-chlorophenyl)imidazo[1,2-a]pyridin-6-yl]phenyl}methanol hydrochloride (1:1) (Compound 26 of the Table)

2.37 g of {3-[2-(4-chlorophenyl)imidazo[1,2-a]pyridin-6-yl]phenyl}methanol are suspended in 80 ml of dichloromethane; 4.26 ml of a 5N solution of hydrochloric acid in 2-propanol are added thereto, dropwise and with stirring, and the mixture is stirred at ambient temperature for 2 hours. The reaction mixture is then concentrated under reduced pressure. The residue solid is taken up with diisopropyl ether and the precipitate is recovered by filtration, washed with dichloromethane and then ethyl acetate and filter-dried. The solid is dissolved at ambient temperature with the minimum amount of methanol and then reprecipitated using diisopropyl ether. The precipitate is recovered by filtration and dried in an oven under reduced pressure at 60° C. 2.23 g of pale yellow solid are obtained. Mp=244-246° C. 1H NMR (DMSO-d6, δ in ppm): 4.59 (s, 2H); from 7.36 to 7.55 (m, 2H); from 7.58 to 7.74 (m, 4H); 7.96 (d, J=9.4 Hz, 1H); 8.05 (m, J=8.7 Hz, 2H); 8.14 (dd, J=9.3 Hz and 1.7 Hz, 1H); 8.70 (s, 1H); 9.15 (m, 1H). M+H=335.

EXAMPLE 7

6-[3-(4-Chlorophenoxymethyl)phenyl]-2-p-tolylimidazo[1,2-a]pyridine (Compound 31 of the Table)

200 mg of [3-(2-p-tolylimidazo[1,2-a]pyridin-6-yl)phenyl]methanol (Example 3) are dissolved in 20 ml of dry tetrahydrofuran, 123 mg of p-chlorophenol, 193 mg of tributylphosphine and 210 mg of 1,1'-azodicarbonyldipiperidine are added thereto and the mixture is left to stir at ambient temperature for 16 h. The solvent is evaporated off under reduced pressure. The residue is taken up with 10 ml of ethyl acetate, the precipitate is removed, the filtrate is concentrated and the residue is purified by chromatography. The solid obtained is taken up with petroleum ether and the precipitate is recovered by filtration and dried under reduced pressure. 52 mg of compound are obtained. Mp=182-184° C. 1H NMR (DMSO-d6, δ in ppm): 2.32 (s, 3H); 5.17 (s, 2H); 7.06 (d, J=7 Hz, 2H); 7.23 (d, J=7.2 Hz, 2H); 7.32 (d, J=7.3 Hz, 2H); from 7.40 to 7.80 (m, 6H); 7.84 (m, J=7.8 Hz, 2H); 8.32 (s, 1H); 8.86 (m, 1H). M+H=425.

EXAMPLE 8

2-{3-[2-(4-Chlorophenyl)imidazo[1,2-a]pyridin-6-yl]phenyl}propan-2-ol (Compound 39 of the Table)

8.1 1-{3-[2-(4-Chlorophenyl)imidazo[1,2-a]pyridin-6-yl]phenyl}ethanone 300 mg of 6-bromo-2-(4-chlorophenyl)imidazo[1,2-a]pyridine (prepared as described in 5.1), 240 mg of 3-acetylboronic acid and 34 mg of tetrakis(triphenylphosphine)palladium are mixed in a microwave tube containing 4.5 ml of acetonitrile, 4.5 ml of toluene and 4.5 ml of a 2M solution of sodium hydrogen carbonate. The tube is placed in a microwave apparatus and irradiated at 150° C. for 15 min. The organic phase is separated, dried and concentrated under reduced pressure. A solid residue is obtained which is triturated in a mixture of 3 ml of dichloromethane and 3 ml of diisopropyl ether for 30 min. The precipitate is recovered by filtration, washed with diisopropyl ether and dried in a desiccator under reduced pressure. 209 mg of compound are obtained. Mp=173-175° C.

8.2 2-{3-[2-(4-Chlorophenyl)imidazo[1,2-a]pyridin-6-yl]phenyl}propan-2-ol

Under a stream of nitrogen, 150 mg of the compound obtained in stage 8.1 are placed in a round-bottomed flask and dissolved in a mixture of 20 ml of dry diethyl ether and 10 ml of dry tetrahydrofuran. The mixture is cooled in an ice bath and 1.3 ml of a 1M solution of methyl magnesium bromide in dibutyl ether are added dropwise. The mixture is left to stir in the ice bath for one hour, and then 5 ml of a saturated aqueous solution of ammonium chloride are added. The organic phase is separated, dried over sodium sulphate and concentrated under reduced pressure. The residue is purified by silica gel chromatography, elution being carried out with a 99/1 dichloromethane/methanol mixture. The solid obtained is triturated in diisopropyl ether and recovered by filtration and then dried in a dessicator under reduced pressure. 65 mg of compound are obtained. Mp=166-168° C. 1H NMR (DMSO-d6, δ in ppm): 1.47 (s, 6H); 5.06 (s, 1H); from 7.33 to 7.69 (m, 7H) 7.78 (m, 1H); 7.97 (m, J=8.5 Hz, 2H); 8.42 (s, 1H); 8.83 (m, 1H). M+H=363.

EXAMPLE 9

{2-[2-(4-Chlorophenyl)imidazo[1,2-a]pyridin-6-yl]phenyl}methanol (Compound 40 of the Table)

Under a stream of nitrogen, 200 mg of 6-bromo-2-(4-chlorophenyl)imidazo[1,2-a]pyridine (prepared as described in 5.1), 148 mg of 2-(hydroxymethyl)phenyl boronic acid and 22.5 mg of tetrakis(triphenylphosphine)palladium are placed in a microwave tube containing a mixture of 3 ml of acetonitrile, 3 ml of toluene and 3 ml of a 2M solution of sodium hydrogen carbonate. The tube is placed in a microwave apparatus and irradiated at 150° C. for 15 min. The organic phase is separated, dried and concentrated under reduced pressure. The residue is purified by silica gel chromatography, elution being carried out with a 98/2 dichloromethane/methanol mixture. The solid obtained is triturated in diisopropyl ether and recovered by filtration and then dried in a dessicator under reduced pressure. 127 mg of compound are obtained. Mp=164-166° C. 1H NMR (DMSO-d6, δ in ppm): 4.44 (d, J=5.6 Hz, 2H); 5.19 (t, J=5.4 Hz, 1H); from 7.25 to 7.64 (m, 8H); 7.98 (m, J=8.3 Hz, 2H); 8.41 (s, 1H); 8.54 (m, 1H). M+H=335.

EXAMPLE 10

{2-[2-(4-Chlorophenyl)imidazo[1,2-a]pyridin-6-yl]phenyl}methanol hydrochloride (1:1) (Compound 41 of the Table)

40 mg of {2-[2-(4-Chlorophenyl)imidazo[1,2-a]pyridin-6-yl]phenyl}methanol are suspended in 1.5 ml of ethanol; 1.79 ml of a 0.1N solution of hydrochloric acid in 2-propanol are added thereto, dropwise and with stirring, and the mixture is stirred at ambient temperature for 30 minutes. The reaction mixture is then concentrated under reduced pressure. The residue solid is taken up with ethanol and the precipitate is recovered by filtration, washed with ethanol and then with diethyl ether and filter-dried. The product is dried in an oven under reduced pressure at 60° C. 17 mg of white solid are obtained. Mp=238-239° C. 1H NMR (DMSO-d6, δ in ppm): 4.50 (s, 2H); from 7.36 to 7.54 (m, 3H); from 7.60 to 7.70 (m, 3H); 7.77 (m, 1H); 7.86 (d, J=7.7 Hz, 1H); 8.14 (d, J=9.2 Hz, 2H); 8.73 (s, 1H); 8.86 (s, 1H). M+H=335.

EXAMPLE 11

Racemic 1-{3-[2-(4-chlorophenyl)imidazo[1,2-a]pyridin-6-yl]phenyl}ethanol (Compound 42 of the Table)

164 mg of sodium borohydride are added portionwise to 150 mg of 1-{3-[2-(4-chloro-phenyl)imidazo[1,2-a]pyridin-6-yl]phenyl}ethanone (compound obtained in 8.1) dissolved in 20 ml of methanol. The mixture is then stirred at ambient temperature for one hour and the solvent is then evaporated off under reduced pressure. The residue is taken up in between water and dichloromethane, the organic phase is separated by settling out and dried over sodium sulphate and the solvent is then evaporated off under reduced pressure. The residue is triturated in diisopropyl ether and recovered by filtration and then dried in a dessicator under reduced pressure. 124 mg of compound are obtained. Mp=174-176° C. 1H NMR (DMSO-d6, δ in ppm): 1.37 (d, J=6.5 Hz, 3H); 4.79 (m, 1H); 5.19 (d, J=4.2 Hz, 1H); from 7.31 to 7.69 (m, 8H); 7.97 (m, J=8.6 Hz, 2H); 8.41 (s, 1H); 8.84 (m, 1H). M+H=349.

EXAMPLE 12

Dextrorotatory enantiomer of 1-{3-[2-(4-chlorophenyl)imidazo[1,2-a]pyridin-6-yl]phenyl}ethanol (Compound 60 of the Table)

263 mg of racemic 1-{3-[2-(4-chlorophenyl)imidazo[1,2-a]pyridin-6-yl]phenyl}ethanol (compound no. 42, Example 11) are loaded onto a ChiralPAK AD DAICEL 20 μm 50×250 mm column. Elution is carried out with an 80/20 mixture of n-heptane and 2-propanol. After crystallization from diisopropyl ether, 115 mg of compound which is the least retained are obtained. Mp=168-170° C. $[\alpha]_D$=+14.3° (c=0.4; MeOH). 1H NMR (DMSO-d6, δ in ppm): 1.36 (d, J=6.2 Hz, 3H); 4.79 (m, 1H); 5.20 (d, J=4.3 Hz, 1H); from 7.31 to 7.69 (m, 8H); 7.97 (m, J=8.6 Hz, 2H); 8.41 (s, 1H); 8.84 (m, 1H). M+H=349.

EXAMPLE 13

Levorotatory enantiomer of 1-{3-[2-(4-chlorophenyl)imidazo[1,2-a]pyridin-6-yl]phenyl}ethanol (Compound 61 of the Table)

By carrying out the process as described in Example 12, and using 263 mg of racemic 1-{3-[2-(4-chlorophenyl)imidazo[1,2-a]pyridin-6-yl]phenyl}ethanol, 112 mg of compound which is the most retained are obtained. Mp=168-170° C. $[\alpha]_D$=−13.6° (c=0.41; MeOH). 1H NMR (DMSO-d6, δ in ppm): 1.37 (d, J=6.6 Hz, 3H); 4.79 (m, 1H); 5.19 (d, J=4.3 Hz, 1H); from 7.31 to 7.69 (m, 8H); 7.97 (m, J=8.7 Hz, 2H); 8.41 (s, 1H); 8.84 (m, 1H). M+H=349.

REPRESENTATIVE EXAMPLES

In this table:
the "o/m/p" column gives the position of substitution of the

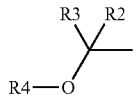

group on the phenyl ring, "ortho/meta/para"; Ph signifies phenyl; $C_5H_9$ signifies cyclopentyl; $C_4H_8N$ signifies pyrrolidin-1-yl;

The "Mp" column gives the melting points of the products in degrees Celsius (° C.) or, when the products have been isolated in the form of an amorphous solid or of an oil, they are characterized by their mass [M+H];

in the "salt/base" column, "-" represents a compound in the form of a free base, whereas "HCl" represents a compound in hydrochloride form and the ratio between parentheses is the (acid:base) ratio.

TABLE 1

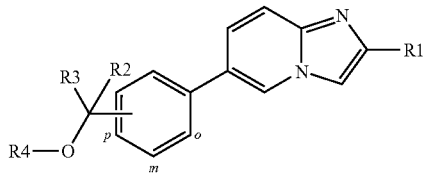

| Ex No. | $R_1$ | o/m/p | $R_2$ | $R_3$ | $R_4$ | Salt | Mp or [M + H] |
|---|---|---|---|---|---|---|---|
| 1 | Ph | para | H | H | H | — | 238-240 |
| 2 | Ph | meta | H | H | H | — | 163-164 |
| 3 | 4-(C₄H₈N)Ph | para | H | H | H | — | 259-261 |
| 4 | 4-Phe-Ph | para | H | H | H | — | 310-312 |
| 5 | 3-CN-Ph | para | H | H | H | — | 205-207 |
| 6 | 3-CN-Ph | meta | H | H | H | — | 184-186 |
| 7 | 3-CN-Ph | meta | H | H | —(CH₂)₂OCH₃ | — | M + H = 384 |
| 8 | 4-CN-Ph | meta | H | H | H | — | 199-201 |
| 9 | 2-naphthyl | meta | H | H | H | — | 161-163 |
| 10 | 4-Me-Ph | meta | H | H | H | — | 171-173 |
| 11 | 4-(C₄H₈N)Ph | meta | H | H | H | — | 181-183 |
| 12 | 3-CF₃O-Ph | meta | H | H | H | — | 154-156 |
| 13 | 4-NO₂-Ph | meta | H | H | H | — | 199-201 |
| 14 | 4-N(C₂H₅)₂-Ph | para | H | H | H | — | 188-190 |
| 15 | 1-naphthyl | meta | H | H | H | — | 306-308 |
| 16 | 2,4-Me₂-Ph | meta | H | H | H | — | 158-160 |
| 17 | 2-naphthyl | meta | H | H | —(CH₂)₂OCH₃ | — | 80-82 |
| 18 | 4-MeO-Ph | meta | H | H | H | — | 214-216 |
| 19 | 3-MeO-Ph | meta | H | H | H | — | 105-107 |
| 20 | 2-MeO-Ph | meta | H | H | H | — | 178-180 |
| 21 | 2,4-(MeO)₂-Ph | meta | H | H | H | — | 191-193 |
| 22 | 4-F-Ph | meta | H | H | H | — | 155-157 |
| 23 | 3,5-F₂-Phe | meta | H | H | H | — | 166-168 |
| 24 | 3-F-5-CF₃-Ph | meta | H | H | H | — | 178-179 |
| 25 | 4-Cl-Ph | meta | H | H | H | — | 181-182 |
| 26 | 4-Cl-Ph | meta | H | H | H | HCl (1:1) | 244-246 |
| 27 | 3-Cl-Ph | meta | H | H | H | — | 260-262 |
| 28 | 4-Cl-3-Me-Ph | meta | H | H | H | — | 157-159 |
| 29 | 3,4-Cl₂-Ph | meta | H | H | H | — | 187-189 |
| 30 | 3-F-Ph | meta | H | H | H | — | 125-127 |
| 31 | 4-Me-Ph | meta | H | H | 4-Cl-Ph | — | 182-184 |
| 32 | 4-Me-Ph | meta | H | H | (CH₃CONH)Ph | — | 191-193 |
| 33 | 4-Me-Ph | meta | H | H | 3-NO₂-Ph | — | 78-80 |
| 34 | 4-Me-Ph | meta | H | H | 4-Me-Ph | — | 141-143 |
| 35 | 4-Me-Ph | meta | H | H | 4-CN-Ph | — | 193-195 |
| 36 | 4-Me-Ph | meta | H | H | 4-(CH₃CO)Ph | — | 186-188 |
| 37 | 4-Me-Ph | meta | H | H | 4-CF₃-Ph | — | 173-175 |
| 38 | 3-F-4-Me-Ph | meta | H | H | H | — | 171-173 |
| 39 | 4-Cl-Ph | meta | Me | Me | H | — | 166-168 |
| 40 | 4-Cl-Ph | ortho | H | H | H | — | 164-166 |
| 41 | 4-Cl-Ph | ortho | H | H | H | HCl (1:1) | 238-239 |
| 42 | 4-Cl-Ph | meta | H | Me | H | — | 174-176 |
| 43 | 2,4-Cl₂-Ph | meta | H | H | H | — | 190-192 |
| 44 | 2,4-F₂-Ph | meta | H | H | H | — | 167-169 |
| 45 | 3,4-F₂-Ph | meta | H | H | H | — | 179-181 |
| 46 | 3,4-F₂-Ph | meta | H | H | H | HCl | 243-246 |

TABLE 1-continued

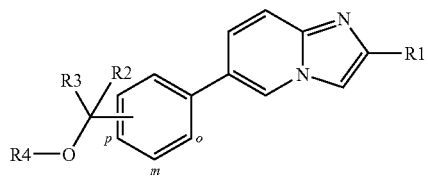

| Ex No. | $R_1$ | o/m/p | $R_2$ | $R_3$ | $R_4$ | Salt | Mp or [M + H] |
|---|---|---|---|---|---|---|---|
| 47 | 2-Cl-Ph | meta | H | H | H | — | 172-174 |
| 48 | 4-CF$_3$-Ph | meta | H | H | H | — | 165-167 |
| 49 | 4-CHF$_2$-Ph | meta | H | H | H | — | 153-155 |
| 50 | 4-Cl-Ph | ortho | H | Me | H | — | 216-218 |
| 51 | 4-Cl-Ph | ortho | H | H | Me | — | 106-108 |
| 52 | 4-Cl-Ph | ortho | H | H | Me | HCl (1:1) | 228-230 |
| 53 | 4-Cl-Ph | para | H | H | Me | — | 104-106 |
| 54 | 4-Cl-Ph | meta | H | C$_2$H$_5$ | H | — | 153-155 |
| 55 | 4-Cl-Ph | meta | H | C$_4$H$_9$ | H | — | 159-161 |
| 56 | 4-Cl-Ph | meta | H | C$_6$H$_{13}$ | H | — | 140-142 |
| 57 | 4-Cl-Ph | meta | H | iBu | H | — | 166-168 |
| 58 | 4-Cl-Ph | meta | H | C$_5$H$_9$ | H | — | M + H = 403 |
| 59 | 4-Cl-Ph | meta | H | Ph | H | — | 242-244 |
| 60 | 4-Cl-Ph | meta | H | Me | H | — | 168-170 |
| 61 | 4-Cl-Ph | meta | H | Me | H | — | 168-170 |
| 62 | 4-Cl-Ph | meta | H | H | Me | — | 135-137 |
| 63 | 4-Cl-Ph | para | H | Me | H | — | 180-182 |
| 64 | 2,4-F$_2$-Ph | meta | H | Me | H | — | 179-181 |
| 65 | 4-F-Ph | meta | H | Me | H | — | 170-172 |
| 66 | 3,4-F$_2$-Ph | meta | H | Me | H | — | 196-198 |
| 67 | 2-Cl-Ph | meta | H | Me | H | — | 156-158 |
| 68 | 3-F-Ph | meta | H | Me | H | — | 166-168 |
| 69 | 3-Cl-Ph | meta | H | Me | H | — | 154-156 |
| 70 | 4-OH-Ph | meta | H | H | H | — | 255.2-256.7 |

Products 60 and 61 are the enantiomers of racemic product 42.

The compounds according to the invention were the subject of pharmacological assays for determining their modulatory effect on Nurr-1/NOT.

Evaluation of the In Vitro Activity on N2A Cells

Assays consisted in measuring the in vitro activity of the compounds of the invention on a cell line (N2A) endogenously expressing the mouse Nurr1 receptor and stably transfected with the NOT binding response element (NBRE) coupled to the luciferase reporter gene. The EC$_{50}$ values are between 0.01 and 1000 nM. The assays were carried out according to the procedure described below.

The Neuro-2A cell line comes from a standard commercial source (ATCC). The Neuro-2A clone was obtained from a spontaneous tumour originating from an A albino mouse strain, by R. J Klebe et col. This Neuro-2A line is subsequently stably transfected with 8NBRE-luciferase. The N2A-8NBRE cells are cultured until confluence in 75 cm$^2$ culture flasks containing DMEM supplemented with 10% of foetal calf serum, 4.5 g/l of glucose and 0.4 mg/ml of geneticin. After a week of culture, the cells are recovered with 0.25% trypsin for 30 seconds and then resuspended in DMEM without phenol red, containing 4.5 g/l of glucose and 10% of Hyclone delipidized serum, and deposited into transparent-bottom 96-well white plates. The cells are deposited at a rate of 60 000 per well in 75 µl for 24 hours before the addition of the products. The products are applied in 25 µl and incubated for a further 24 hours. On the day of the measurement, an equivalent volume (100 µl) of Steadylite are added to each well and then left for a period of 30 minutes in order to obtain complete cell lysis and maximum signal production. The plates are subsequently measured in a luminescence counter for microplates after having been sealed with an adhesive film. The products are prepared in the form of a stock solution at 10$^{-2}$M and then diluted in 100% of DMSO. Each product concentration is prediluted in culture medium before incubation with the cells, thus containing 0.625% final concentration of DMSO.

For example, compounds No. 17, 31, 39 and 40 of the table showed an EC$_{50}$ value of 3.6 nM, 14 nM, 0.7 nM and 0.7 nM, respectively.

Evaluation of the Binding to the Human NOT Receptor

The direct binding between compounds of the invention and the human NOT receptor was evaluated using SPR (surface plasmon resonance) technology. In this assay, the protein is immobilized covalently to the matrix and the molecule to be studied is injected into the chamber containing the sensor chip (biosensor or reactive surface). The signal is directly proportional to the amount of product bound to the protein. The binding assays were carried out in a BIACORE S51 instrument (Biacore Inc., Piscataway N.J.). The GST-NOT (NOT-FL) whole protein was provided by Invitrogen (PV3265).

The NOT ligand-binding domain (His-Thr-NOT 329-598) was expressed and purified as described in Nature 423, 555-560. The two proteins, diluted to a concentration of 20 µg/ml in an acetate buffer, pH 5.0, containing 5 mM of DTT, were immobilized on a carboxymethyl 5' dextran surface (CM5 sensor chip, Biacore Inc.) by amine coupling according to the protocol recommended by Biacore, elution being carried with an HBS-N buffer (10 mM HEPES, 0.15 M NaCl, 3 mM EDTA, pH 7.4). Approximately 10000-15000 resonance units (RU) of the proteins are captured on the surface of the CM5 sensor chip. The stock solutions of the compounds to be studied, at 1.5 mM in DMSO, are serially diluted in elution buffer (50 mM HEPES pH 8; 150 mM NaCl; 10 mM $MgCl_2$; 2% DMSO, 1 mM DTT) to concentrations ranging from 3.75 to 0.1 μM. Each product concentration is injected at 4° C. for 1 minute at 30 μl/min. The dissociation was recorded for 5 minutes without any other procedure for regenerating the surface. The signals obtained are corrected by testing each product concentration on an unmodified dextran surface (blank). The signal due to the migration buffer is deducted from the total signal ("double referencing") as is the effect of the DMSO. The signal analysis is carried out using the Biacore S51 analytical software (version 1.2.1). The compounds are subsequently classified according to their maximum binding level and to kinetic parameters for binding to the immobilized protein.

By way of example, compound No. 9 has a high affinity and compound No. 10 has a medium affinity.

It therefore appears that the compounds according to the invention have a NOT-modulating effect.

The compounds according to the invention can therefore be used for the preparation of medicaments for their therapeutic use in the treatment or prevention of diseases involving NOT receptors.

Thus, according to another of its aspects, a subject of the invention is medicaments which comprise a compound of formula (I), or an addition salt of the latter with a pharmaceutically acceptable acid.

These medicaments find their use in therapeutics, in particular in the treatment and prevention of neurodegenerative diseases, such as, for example, Parkinson's Disease, Alzheimer's Disease, tauopathies (for example, progressive supranuclear palsy, frontotemporal dementia, corticobasal degeneration, Pick's Disease), multiple sclerosis; cerebral traumas such as ischemia and cranial traumas and epilepsy; psychiatric diseases such as schizophrenia, depression, substance dependency, attention deficit hyperactivity disorders; inflammatory diseases such as vascular pathologies, atherosclerosis, joint inflammations, arthrosis, rheumatoid arthritis, osteoarthritis, allergic inflammatory diseases such as asthma, and finally, the treatment of osteoporosis or cancers.

These compounds could also be used as a treatment associated with stem cell transplants and/or grafts.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are selected according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its salt, can be administered in unit administration form, as a mixture with conventional pharmaceutical excipients, to animals or to human beings for the prophylaxis or the treatment of the disorders or the diseases above.

The appropriate unit administration forms include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form can comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

There may be specific cases where higher or lower dosages are appropriate; such dosages do not depart from the scope of the invention. According to customary practice, the dosage appropriate for each patient is determined by the physician according to the method of administration and the weight and the response of said patient.

According to another of its aspects, the present invention also relates to a method for treating the pathologies indicated above, which comprises the administration, to a patient, of an effective dose of a compound according to the invention, or one of its pharmaceutically acceptable salts.

We claim:
1. A compound of formula (I):

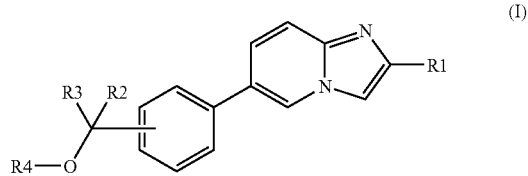

wherein:
$R_1$ is phenyl or naphthyl, each of which is optionally substituted one or more times independently by halogen, $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, $(C_3-C_7)$cycloalkoxy, $(C_3-C_7)$cycloalkyl$(C_1-C_3)$alkyleneoxy, halo$(C_1-C_6)$alkoxy, $(C_1-C_6)$thioalkyl, —S(O)$(C_1-C_6)$alkyl, —S(O)$_2(C_1-C_6$-alkyl), hydroxyl, cyano, nitro, hydroxy$(C_1-C_6)$alkylene, NRaRb$(C_1-C_6)$alkylene, $(C_1-C_6)$alkoxy$(C_1-C_6)$alkyleneoxy, NRaRb, CONRaRb, $SO_2$NRaRb, NRcCORd, OC(O)NRaRb, NRcC(O)ORe, NRcSO$_2$Re, aryl$(C_1-C_6)$alkylene, aryl or heteroaryl, wherein the aryl and heteroaryl are optionally substituted one or more times independently by halogen, $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano;

$R_2$ and $R_3$ are, independently of one another,
hydrogen,
$(C_1-C_6)$alkyl, $(C_3-C_7)$cycloalkyl or $(C_3-C_7)$cycloalkyl$(C_1-C_3)$alkylene group, each of which is optionally substituted with an Rf group, or
aryl, which is optionally substituted one or more times independently by halogen, $C_1-C_6)$alkyl, $(C_3-C_7)$cycloalkyl, $(C_3-C_7)$cycloalkyl$(C_1-C_3)$alkylene, halo $(C_1-C_6)$alkyl, $(C_1-C_6)$alkoxy, halo$(C_1-C_6)$alkoxy, NRaRb, hydroxyl, nitro or cyano;

R<sub>4</sub> is hydrogen,
  ($C_1$-$C_6$)alkyl, ($C_3$-$C_7$)cycloalkyl or ($C_3$-$C_7$)cycloalkyl($C_1$-$C_3$)alkylene group, each of which is optionally substituted with an Rf group, or
  aryl, which is optionally substituted one or more times independently by halogen, ($C_1$-$C_6$)alkyl, ($C_3$-$C_7$)cycloalkyl, ($C_3$-$C_7$)cycloalkyl($C_1$-$C_3$)alkylene, halo($C_1$-$C_6$)alkyl, ($C_1$-$C_6$)alkoxy, ($C_3$-$C_7$)cycloalkoxy, ($C_3$-$C_7$)cycloalkyl($C_1$-$C_3$)alkyleneoxy, halo($C_1$-$C_6$)alkoxy, NRaRb, hydroxyl, nitro, cyano, ($C_1$-$C_6$)alkyl(CO)—, CONRaRb, NRcCORd, OC(O)NRaRb, NRcC(O)Ore, or aryl that is optionally substituted one or more times independently by halogen, ($C_1$-$C_6$)alkyl, ($C_3$-$C_7$)cycloalkyl, ($C_3$-$C_7$)cycloalkyl($C_1$-$C_3$)alkylene, halo($C_1$-$C_6$)alkyl, ($C_1$-$C_6$)alkoxy, halo($C_1$-$C_6$)alkoxy, NRaRb, hydroxyl, nitro or cyano;

Ra and Rb are, independently of one another,
  Hydrogen, ($C_1$-$C_6$)alkyl, ($C_3$-$C_7$)cycloalkyl, ($C_3$-$C_7$)cycloalkyl($C_1$-$C_3$)alkylene, aryl($C_1$-$C_6$)alkylene or aryl, or
  Ra and Rb taken together with the nitrogen atom to which they are attached form azetidine, pyrrolidine, piperidine, azepine, morpholine, thiomorpholine, piperazine or homopiperazine, each of which is optionally substituted by ($C_1$-$C_6$)alkyl, ($C_3$-$C_7$)cycloalkyl, ($C_3$-$C_7$)cycloalkyl($C_1$-$C_6$)alkylene, aryl or aryl($C_1$-$C_6$)alkylene;

Rc and Rd are, independently of one another,
  Hydrogen, ($C_1$-$C_6$)alkyl, ($C_3$-$C_7$)cycloalkyl, ($C_3$-$C_7$)cycloalkyl($C_1$-$C_3$)alkylene, aryl($C_1$-$C_6$)alkylene or aryl, or
  Rc and Rd together form ($C_2$-$C_5$)alkylene;

Re is ($C_1$-$C_6$)alkyl, ($C_3$-$C_7$)cycloalkyl, ($C_3$-$C_7$)cycloalkyl($C_1$-$C_3$)alkylene, aryl($C_1$-$C_6$)alkylene or aryl, or Rc and Re together form a ($C_2$-$C_5$)alkylene group; and Rf is halogen, ($C_1$-$C_6$)alkoxy, halo($C_1$-$C_6$)alkoxy, ($C_3$-$C_7$)cycloalkoxy, ($C_3$-$C_7$)cycloalkyl($C_1$-$C_6$)alkyleneoxy, hydroxyl, cyano, NRaRb, C(O)NRaRb, NRcCORd, OC(O)NRaRb, NRcCOORe, SO$_2$NRaRb, NRcSO$_2$Re, aryl($C_1$-$C_6$)alkylene or aryl, wherein the aryl is optionally substituted one or more times independently by halogen, ($C_1$-$C_6$)alkyl, ($C_3$-$C_7$)cycloalkyl, ($C_3$-$C_7$)cycloalkyl($C_1$-$C_3$)alkylene, halo($C_1$-$C_6$)alkyl, ($C_1$-$C_6$)alkoxy, halo($C_1$-$C_6$)alkoxy, NRaRb, hydroxyl, nitro or cyano;

or an addition salt with an acid thereof.

2. The compound according to claim 1, wherein:
R<sub>1</sub> is naphthyl or phenyl, each of which is optionally substituted one or more times independently by halogen, ($C_1$-$C_6$)alkyl, ($C_3$-$C_7$)cycloalkyl, ($C_3$-$C_7$)cycloalkyl($C_1$-$C_6$)alkylene, ($C_1$-$C_6$)alkoxy, ($C_3$-$C_7$)cycloalkyl($C_1$-$C_6$)alkoxy, hydroxyl, cyano, nitro, NRaRb, hydroxy($C_1$-$C_6$)alkyl, ($C_1$-$C_6$)alkoxy($C_1$-$C_6$)alkyl, halo($C_1$-$C_6$)alkyl, halo($C_1$-$C_6$)alkoxy or aryl, wherein the aryl is optionally substituted one or more times independently by halogen, ($C_1$-$C_6$)alkyl, ($C_3$-$C_7$)cycloalkyl, ($C_3$-$C_7$)cycloalkyl($C_1$-$C_3$)alkylene, halo($C_1$-$C_6$)alkyl, ($C_1$-$C_6$)alkoxy, halo($C_1$-$C_6$)alkoxy, NRaRb, hydroxyl, nitro or cyano;

or an addition salt with an acid thereof.

3. The compound according to claim 1, wherein:
R<sub>2</sub> and R<sub>3</sub> are, independently of one another,
  hydrogen, or
  ($C_1$-$C_6$)alkyl, ($C_3$-$C_7$)cycloalkyl or ($C_3$-$C_7$)cycloalkyl($C_1$-$C_3$)alkylene, each of which is optionally substituted with an Rf group; and R<sub>4</sub> is hydrogen,
  ($C_1$-$C_6$)alkyl, ($C_3$-$C_7$)cycloalkyl or ($C_3$-$C_7$)cycloalkyl($C_1$-$C_3$)alkylene, each of which is optionally substituted with an Rf group, or
  aryl, which is optionally substituted one or more times independently by halogen, ($C_1$-$C_6$)alkyl, ($C_3$-$C_7$)cycloalkyl, ($C_3$-$C_7$)cycloalkyl($C_1$-$C_3$)alkylene, halo($C_1$-$C_6$)alkyl, ($C_1$-$C_6$)alkoxy, ($C_3$-$C_7$)cycloalkoxy, ($C_3$-$C_7$)cycloalkyl($C_1$-$C_3$)alkyleneoxy, halo($C_1$-$C_6$)alkoxy, NRaRb, hydroxyl, nitro, cyano, ($C_1$-$C_6$)alkyl(CO)—, NRcCORd, or aryl that is optionally substituted one or more times independently by halogen, ($C_1$-$C_6$)alkyl, ($C_3$-$C_7$)cycloalkyl, ($C_3$-$C_7$)cycloalkyl($C_1$-$C_3$)alkylene, halo($C_1$-$C_6$)alkyl, ($C_1$-$C_6$)alkoxy, halo($C_1$-$C_6$)alkoxy, NRaRb, hydroxyl, nitro or cyano;

or an addition salt with an acid thereof.

4. The compound according to claim 1, wherein:
the substituent

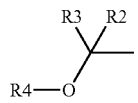

is in the meta-position on the phenyl; or an addition salt with an acid thereof.

5. The compound according to claim 1, wherein:
R<sub>4</sub> is hydrogen; and
R<sub>2</sub> and R<sub>3</sub> are, independently of one another,
  hydrogen, or
  ($C_1$-$C_6$)alkyl, ($C_3$-$C_7$)cycloalkyl or ($C_3$-$C_7$)cycloalkyl($C_1$-$C_3$)alkylene, each of which is optionally substituted with an Rf group;

or an addition salt with an acid thereof.

6. The compound according to claim 1, wherein:
R<sub>1</sub> is naphthyl or phenyl, each of which is optionally substituted one or more times independently by halogen, ($C_1$-$C_6$)alkyl, ($C_3$-$C_7$)cycloalkyl, ($C_3$-$C_7$)cycloalkyl($C_1$-$C_6$)alkylene, ($C_1$-$C_6$)alkoxy, ($C_3$-$C_7$)cycloalkyl($C_1$-$C_6$)alkoxy, hydroxyl, cyano, nitro, NRaRb, hydroxy($C_1$-$C_6$)alkyl, ($C_1$-$C_6$)alkoxy($C_1$-$C_6$)alkyl, halo($C_1$-$C_6$)alkyl, halo($C_1$-$C_6$)alkoxy or aryl, wherein the aryl is optionally substituted one or more times independently by halogen, ($C_1$-$C_6$)alkyl, ($C_3$-$C_7$)cycloalkyl, ($C_3$-$C_7$)cyclo-alkyl($C_1$-$C_3$)alkylene, halo($C_1$-$C_6$)alkyl, ($C_1$-$C_6$)alkoxy, halo($C_1$-$C_6$)alkoxy, NRaRb, hydroxyl, nitro or cyano;

R<sub>2</sub> and R<sub>3</sub> are, independently of one another,
  hydrogen,
  ($C_1$-$C_6$)alkyl, ($C_3$-$C_7$)cycloalkyl or ($C_3$-$C_7$)cycloalkyl($C_1$-$C_3$)alkylene, each of which is optionally substituted with an Rf group, or
  aryl, which is optionally substituted one or more times independently by halogen, ($C_1$-$C_6$)alkyl, ($C_3$-$C_7$)cycloalkyl, ($C_3$-$C_7$)cycloalkyl($C_1$-$C_3$)alkylene, halo($C_1$-$C_6$)alkyl, ($C_1$-$C_6$)alkoxy, halo($C_1$-$C_6$)alkoxy, NRaRb, hydroxyl, nitro or cyano; and R<sub>4</sub> is hydrogen,
  ($C_1$-$C_6$)alkyl, ($C_3$-$C_7$)cycloalkyl or ($C_3$-$C_7$)cycloalkyl($C_1$-$C_3$)alkylene, each of which is optionally substituted with an Rf group, or
  aryl, which is optionally substituted one or more times independently by halogen, ($C_1$-$C_6$)alkyl, ($C_3$-$C_7$)cycloalkyl, ($C_3$-$C_7$)cycloalkyl($C_1$-$C_3$)alkylene, halo($C_1$-$C_6$)alkyl, nitro, cyano, ($C_1$-$C_6$)alkyl(CO)— or NRcCORd group;

or an addition salt with an acid thereof.

7. The compound according to claim 1, wherein:
R₁ is naphthyl or phenyl, each of which is optionally substituted one or more times independently by halogen, $(C_1-C_6)$alkyl, $(C_3-C_7)$cycloalkyl, $(C_3-C_7)$cycloalkyl$(C_1-C_6)$alkylene, $(C_1-C_6)$alkoxy, $(C_3-C_7)$cycloalkyl$(C_1-C_6)$alkoxy, hydroxyl, cyano, nitro, NRaRb, hydroxy$(C_1-C_6)$alkyl, $(C_1-C_6)$alkoxy$(C_1-C_6)$alkyl, halo$(C_1-C_6)$alkyl or halo$(C_1-C_6)$alkoxy;

R₂ and R₃ are, independently of one another,
 hydrogen,
 $(C_1-C_6)$alkyl, $(C_3-C_7)$cycloalkyl or $(C_3-C_7)$cycloalkyl$(C_1-C_3)$alkylene, each of which is optionally substituted with an Rf group, or
 aryl, wherein the aryl is optionally substituted one or more times independently by halogen, $(C_1-C_6)$alkyl, $(C_3-C_7)$cycloalkyl, $(C_3-C_7)$cycloalkyl$(C_1-C_3)$alkylene, halo$(C_1-C_6)$alkyl, $(C_1-C_6)$alkoxy, halo$(C_1-C_6)$alkoxy, NRaRb, hydroxyl, nitro or cyano; and R₄ is hydrogen,
 $(C_1-C_6)$alkyl, $(C_3-C_7)$cycloalkyl or $(C_3-C_7)$cycloalkyl$(C_1-C_3)$alkylene, each of which is optionally substituted with an Rf group, or
 aryl, wherein the aryl is optionally substituted one or more times independently by halogen, $(C_1-C_6)$alkyl, $(C_3-C_7)$cycloalkyl, $(C_3-C_7)$cycloalkyl$(C_1-C_3)$alkylene, halo$(C_1-C_6)$alkyl, nitro, cyano, $(C_1-C_6)$alkyl (CO)— or NRcCORd;
or an addition salt with an acid thereof.

8. The compound according to claim 1, which is:
[4-(2-phenylimidazo[1,2-a]pyridin-6-yl)phenyl]methanol,
[3-(2-phenylimidazo[1,2-a]pyridin-6-yl)phenyl]methanol,
{4-[2-(4-pyrrolidin-1-ylphenyl)imidazo[1,2-a]pyridin-6-yl]phenyl}methanol,
[4-(2-biphenyl-4-ylimidazo[1,2-a]pyridin-6-yl)phenyl]methanol,
3-[6-(4-hydroxymethylphenyl)imidazo[1,2-a]pyridin-2-yl]benzonitrile,
3-[6-(3-hydroxymethylphenyl)imidazo[1,2-a]pyridin-2-yl]benzonitrile,
3-{6-[3-(2-methoxyethoxymethyl)phenyl]imidazo[1,2-a]pyridin-2-yl}benzonitrile,
4-[6-(3-hydroxymethylphenyl)imidazo[1,2-a]pyridin-2-yl]benzonitrile,
[3-[2-(naphthalen-2-yl)imidazo[1,2-a]pyridin-6-yl]phenyl]methanol,
[3-(2-p-tolylimidazo[1,2-a]pyridin-6-yl)phenyl]methanol,
{3-[2-(4-pyrrolidin-1-ylphenyl)imidazo[1,2-a]pyridin-6-yl]phenyl}methanol,
{3-[2-(3-trifluoromethoxyphenyl)imidazo[1,2-a]pyridin-6-yl]phenyl}methanol,
{3-[2-(4-nitrophenyl)imidazo[1,2-a]pyridin-6-yl]phenyl}methanol,
{4-[2-(4-diethylaminophenyl)imidazo[1,2-a]pyridin-6-yl]phenyl}methanol,
[3-(2-naphthalen-1-ylimidazo[1,2-a]pyridin-6-yl)phenyl]methanol,
{3-[2-(2,4-dimethylphenyl)imidazo[1,2-a]pyridin-6-yl]phenyl}methanol,
6-[3-(2-methoxyethoxymethyl)phenyl]-2-naphthalen-2-ylimidazo[1,2-a]pyridine,
{3-[2-(4-methoxyphenyl)imidazo[1,2-a]pyridin-6-yl]phenyl}methanol,
{3-[2-(3-methoxyphenyl)imidazo[1,2-a]pyridin-6-yl]phenyl}methanol,
{3-[2-(2-methoxyphenyl)imidazo[1,2-a]pyridin-6-yl]phenyl}methanol,
{3-[2-(2,4-dimethoxyphenyl)imidazo[1,2-a]pyridin-6-yl]phenyl}methanol,
{3-[2-(4-fluorophenyl)imidazo[1,2-a]pyridin-6-yl]phenyl}methanol,
{3-[2-(3,5-difluorophenyl)imidazo[1,2-a]pyridin-6-yl]phenyl}methanol,
{3-[2-(3-fluoro-5-trifluoromethylphenyl)imidazo[1,2-a]pyridin-6-yl]phenyl}methanol,
{3-[2-(4-chlorophenyl)imidazo[1,2-a]pyridin-6-yl]phenyl}methanol,
{3-[2-(4-chlorophenyl)imidazo[1,2-a]pyridin-6-yl]phenyl}methanol hydrochloride (1:1),
{3-[2-(3-chlorophenyl)imidazo[1,2-a]pyridin-6-yl]phenyl}methanol,
{3-[2-(4-chloro-3-methylphenyl)imidazo[1,2-a]pyridin-6-yl]phenyl}methanol,
{3-[2-(3,4-dichlorophenyl)imidazo[1,2-a]pyridin-6-yl]phenyl}methanol,
{3-[2-(3-fluorophenyl)imidazo[1,2-a]pyridin-6-yl]phenyl}methanol,
6-[3-(4-chlorophenoxymethyl)phenyl]-2-p-tolylimidazo[1,2-a]pyridine,
N-{4-[3-(2-p-tolylimidazo[1,2-a]pyridin-6-yl)benzyloxy]phenyl}acetamide,
6-[3-(3-nitrophenoxymethyl)phenyl]-2-p-tolylimidazo[1,2-a]pyridine,
6-[3-(4-methylphenoxymethyl)phenyl]-2-p-tolylimidazo[1,2-a]pyridine,
4-[3-(2-p-tolylimidazo[1,2-a]pyridin-6-yl)benzyloxy]benzonitrile,
1-{4-[3-(2-p-tolylimidazo[1,2-a]pyridin-6-yl)benzyloxy]phenyl}ethanone,
6-[3-(4-trifluoromethylphenoxymethyl)phenyl]-2-p-tolylimidazo[1,2-a]pyridine,
{3-[2-(3-fluoro-4-methylphenyl)imidazo[1,2-a]pyridin-6-yl]phenyl}methanol,
2-{3-[2-(4-chlorophenyl)imidazo[1,2-a]pyridin-6-yl]phenyl}propan-2-ol,
{2-[2-(4-chlorophenyl)imidazo[1,2-a]pyridin-6-yl]phenyl}methanol,
{2-[2-(4-chlorophenyl)imidazo[1,2-a]pyridin-6-yl]phenyl}methanol hydrochloride (1:1),
racemic 1-{3-[2-(4-chlorophenyl)imidazo[1,2-a]pyridin-6-yl]phenyl}ethanol,
{3-[2-(2,4-dichlorophenyl)imidazo[1,2-a]pyridin-6-yl]phenyl}methanol,
{3-[2-(2,4-difluorophenyl)imidazo[1,2-a]pyridin-6-yl]phenyl}methanol,
{3-[2-(3,4-difluorophenyl)imidazo[1,2-a]pyridin-6-yl]phenyl}methanol,
{3-[2-(3,4-difluorophenyl)imidazo[1,2-a]pyridin-6-yl]phenyl}methanol hydrochloride (1:1),
{3-[2-(2-chlorophenyl)imidazo[1,2-a]pyridin-6-yl]phenyl}methanol,
{3-[2-(4-trifluoromethylphenyl)imidazo[1,2-a]pyridin-6-yl]phenyl}methanol,
{3-[2-(4-(difluoromethyl)phenyl)imidazo[1,2-a]pyridin-6-yl]phenyl}methanol,
racemic 1-{2-[2-(4-chlorophenyl)imidazo[1,2-a]pyridin-6-yl]phenyl}ethanol,
2-(4-chlorophenyl)-6-(2-methoxymethylphenyl)imidazo[1,2-a]pyridine,
2-(4-chlorophenyl)-6-(2-methoxymethylphenyl)imidazo[1,2-a]pyridine hydrochloride (1:1), 2-(4-chlorophenyl)-6-(4-methoxymethylphenyl)imidazo[1,2-a]pyridine,
racemic 1-{3-[2-(4-chlorophenyl)imidazo[1,2-a]pyridin-6-yl]phenyl}propan-1-ol,
racemic 1-{3-[2-(4-chlorophenyl)imidazo[1,2-a]pyridin-6-yl]phenyl}pentan-1-ol,
racemic 1-{3-[2-(4-chlorophenyl)imidazo[1,2-a]pyridin-6-yl]phenyl} heptan-1-ol,
racemic 1-{3-[2-(4-chlorophenyl)imidazo[1,2-a]pyridin-6-yl]phenyl}-3-methylbutan-1-ol,
racemic {3-[2-(4-chlorophenyl)imidazo[1,2-a]pyridin-6-yl]phenyl}cyclopentylmethanol,
racemic {3-[2-(4-chlorophenyl)imidazo[1,2-a]pyridin-6-yl]phenyl}phenylmethanol,
dextrorotatory enantiomer of 1-{3-[2-(4-chlorophenyl)imidazo[1,2-a]pyridin-6-yl]phenyl}ethanol,
levorotatory enantiomer of 1-{3-[2-(4-chlorophenyl)imidazo[1,2-a]pyridin-6-yl]phenyl}ethanol,
2-(4-chlorophenyl)-6-(3-methoxymethylphenyl)imidazo[1,2-a]pyridine,
racemic 1-{4-[2-(4-chlorophenyl)imidazo[1,2-a]pyridin-6-yl]phenyl}ethanol,
racemic 1-{3-[2-(2,4-difluorophenyl)imidazo[1,2-a]pyridin-6-yl]phenyl}ethanol,
racemic 1-{3-[2-(4-fluorophenyl)imidazo[1,2-a]pyridin-6-yl]phenyl}ethanol,
racemic 1-{3-[2-(3,4-difluorophenyl)imidazo[1,2-a]pyridin-6-yl]phenyl}ethanol,
racemic 1-{3-[2-(2-chlorophenyl)imidazo[1,2-a]pyridin-6-yl]phenyl}ethanol,
racemic 1-{3-[2-(3-fluorophenyl)imidazo[1,2-a]pyridin-6-yl]phenyl}ethanol,
racemic 1-{3-[2-(3-chlorophenyl)imidazo[1,2-a]pyridin-6-yl]phenyl}ethanol, or
4-[6-(3-hydroxymethylphenyl)imidazo[1,2-a]pyridin-2-yl]phenol,
or an addition salt with an acid thereof.

9. A pharmaceutical composition comprising the compound according to claim 1 or a pharmaceutically acceptable addition salt with an acid thereof, in combination with at least one pharmaceutically acceptable excipient.

10. A pharmaceutical composition comprising the compound according to claim 2 or a pharmaceutically acceptable addition salt with an acid thereof, in combination with at least one pharmaceutically acceptable excipient.

11. A pharmaceutical composition comprising the compound according to claim 3 or a pharmaceutically acceptable addition salt with an acid thereof, in combination with at least one pharmaceutically acceptable excipient.

12. A pharmaceutical composition comprising the compound according to claim 4 or a pharmaceutically acceptable addition salt with an acid thereof, in combination with at least one pharmaceutically acceptable excipient.

13. A pharmaceutical composition comprising the compound according to claim 5 or a pharmaceutically acceptable addition salt with an acid thereof, in combination with at least one pharmaceutically acceptable excipient.

14. A pharmaceutical composition comprising the compound according to claim 6 or a pharmaceutically acceptable addition salt with an acid thereof, in combination with at least one pharmaceutically acceptable excipient.

15. A pharmaceutical composition comprising the compound according to claim 7 or a pharmaceutically acceptable addition salt with an acid thereof, in combination with at least one pharmaceutically acceptable excipient.

16. A pharmaceutical composition comprising the compound according to claim 8 or a pharmaceutically acceptable addition salt with an acid thereof, in combination with at least one pharmaceutically acceptable excipient.

17. A process for preparing the compound according to claim 1, comprising coupling a 2-arylimidazopyridine of formula (II),

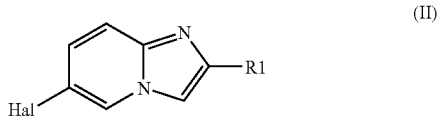

wherein Hal is halogen,
with a derivative of formula (III),

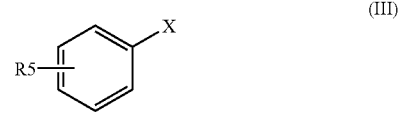

wherein X is a derivative of boron or tin, and R5 is a

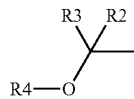

group, in the presence of a metal catalyst.

* * * * *